United States Patent
Schuetz et al.

(10) Patent No.: US 10,675,399 B2
(45) Date of Patent: Jun. 9, 2020

(54) POLYMERIC WHOLE BLOOD HOLLOW FIBER MEMBRANE FILTER MEDIUM AND USE THEREOF FOR SEPARATING BLOOD PLASMA/SERUM FROM WHOLE BLOOD

(71) Applicant: Mann+Hummel GMBH, Ludwigsburg (DE)

(72) Inventors: Steffen Schuetz, Bietigheim-Bissingen (DE); Heike Rupp, Stuttgart (DE); Dagmar Winkler, Filderstadt (DE); Frank Ehlen, Neunkirchen (DE)

(73) Assignee: MANN+HUMMEL GmbH, Ludwigsburg (DE)

( * ) Notice: Subject to any disclaimer, the term of this patent is extended or adjusted under 35 U.S.C. 154(b) by 173 days.

(21) Appl. No.: 14/938,381

(22) Filed: Nov. 11, 2015

(65) Prior Publication Data

US 2016/0074569 A1    Mar. 17, 2016

Related U.S. Application Data

(63) Continuation of application No. PCT/EP2014/063602, filed on Jun. 26, 2014.

(30) Foreign Application Priority Data

Jun. 27, 2013 (DE) .................. 10 2013 010 724

(51) Int. Cl.
*A61M 1/34* (2006.01)
*B01D 63/02* (2006.01)
(Continued)

(52) U.S. Cl.
CPC ............... *A61M 1/34* (2013.01); *A61M 1/16* (2013.01); *A61M 1/3482* (2014.02);
(Continued)

(58) Field of Classification Search
CPC .... B01D 69/08; B01D 69/081; B01D 69/087; B01D 69/02; B01D 2325/02; B01D 2325/04; B01D 2325/14; B01D 2325/20; B01D 67/0088; B01D 67/0093; B01D 71/26; B01D 71/34; B01D 71/40;
(Continued)

(56) References Cited

U.S. PATENT DOCUMENTS 5,053,048 A * 10/1991 Pinchuk .............. A61L 33/0029
                                                           128/DIG. 21
5,674,394 A * 10/1997 Whitmore ........... A61M 1/3496
                                                           210/321.6
(Continued)

FOREIGN PATENT DOCUMENTS

DE      10332116 B3    2/2005
EP      0785012 A1 *   7/1997

*Primary Examiner* — John Kim
(74) *Attorney, Agent, or Firm* — James Hasselbeck

(57) ABSTRACT

A whole blood hollow fiber membrane filter medium is made of a polymeric material having pores of a pore size that ensures permeability to blood plasma or serum but retains blood cells. The whole blood hollow fiber membrane filter medium is used for filtering a whole blood sample so that blood plasma or serum passes through the whole blood hollow fiber membrane filter medium and blood cells are retained. The obtained blood plasma shows no hemolysis.

34 Claims, 2 Drawing Sheets

(51) Int. Cl.
| | |
|---|---|
| *B01D 69/02* | (2006.01) |
| *B01D 69/08* | (2006.01) |
| *B01D 67/00* | (2006.01) |
| *B01D 71/26* | (2006.01) |
| *B01D 71/34* | (2006.01) |
| *B01D 71/40* | (2006.01) |
| *B01D 71/42* | (2006.01) |
| *B01D 71/68* | (2006.01) |
| *G01N 1/40* | (2006.01) |
| *G01N 33/49* | (2006.01) |
| *B01D 71/56* | (2006.01) |
| *A61M 1/36* | (2006.01) |
| *A61M 1/16* | (2006.01) |

(52) U.S. Cl.
CPC ........ *A61M 1/3496* (2013.01); *A61M 1/3633* (2013.01); *B01D 63/02* (2013.01); *B01D 63/021* (2013.01); *B01D 67/0088* (2013.01); *B01D 67/0093* (2013.01); *B01D 69/02* (2013.01); *B01D 69/08* (2013.01); *B01D 69/081* (2013.01); *B01D 69/087* (2013.01); *B01D 71/26* (2013.01); *B01D 71/34* (2013.01); *B01D 71/40* (2013.01); *B01D 71/42* (2013.01); *B01D 71/56* (2013.01); *B01D 71/68* (2013.01); *G01N 1/4005* (2013.01); *G01N 33/491* (2013.01); *B01D 2325/02* (2013.01); *B01D 2325/04* (2013.01); *B01D 2325/14* (2013.01); *B01D 2325/20* (2013.01)

(58) Field of Classification Search
CPC ........ B01D 71/42; B01D 71/56; B01D 71/68; B01D 63/02; B01D 63/021; A61M 1/16; A61M 1/34; A61M 1/3482; A61M 1/3496; A61M 1/3633; G01N 33/491; G01N 1/4005
See application file for complete search history.

(56) References Cited

U.S. PATENT DOCUMENTS

| | | | |
|---|---|---|---|
| 5,919,356 A * | 7/1999 | Hood | B01D 61/18 |
| | | | 210/136 |
| 5,979,669 A * | 11/1999 | Kitajima | B01D 39/2017 |
| | | | 210/247 |
| 6,214,232 B1 | 4/2001 | Baurmeister et al. | |
| 6,270,674 B1 | 8/2001 | Baurmeister et al. | |
| 2006/0108288 A1 * | 5/2006 | Oishi | A61M 1/3472 |
| | | | 210/639 |
| 2006/0184112 A1 * | 8/2006 | Horn | A61L 29/126 |
| | | | 604/103.08 |
| 2012/0226258 A1 | 9/2012 | Otto | |

* cited by examiner

POLYMERIC WHOLE BLOOD HOLLOW FIBER MEMBRANE FILTER MEDIUM AND USE THEREOF FOR SEPARATING BLOOD PLASMA/SERUM FROM WHOLE BLOOD

CROSS-REFERENCE TO RELATED APPLICATIONS

This application is a continuation application of international application No. PCT/EP2014/063602 having an international filing date of 26 Jun. 2014 and designating the United States, the international application claiming a priority date of 27 Jun. 2013, based on prior filed German patent application No. 10 2013 010 724.5, the entire contents of the aforesaid international application and the aforesaid German patent application being incorporated herein by reference

BACKGROUND OF THE INVENTION

The present invention relates to a whole blood hollow fiber membrane filter medium including a polymeric material having a pore size ensuring permeability to the liquid part of whole blood, preferably to blood plasma or serum, but retaining blood cells and to the use of said whole blood hollow fiber membrane filter medium for separating blood plasma or serum from whole blood.

In medical technology, various kinds of blood and plasma/serum separation and treatment processes are known and state-of-the-art. The most common method to separate blood cells from the liquid part of the blood is centrifugation.

In transfusion medicine, filters are used to remove leucocytes from transfusion blood and to remove blood clots and particles. Furthermore, artery filters are applied during surgeries, e.g. to remove blood clots, particles and gas bubbles. Plasmapheresis filters are used to clean or to substitute plasma from patients, which is poisoned by bacteria, viruses or further components, which are dangerous to life, with artificial blood plasma or plasma from donators.

Moreover, microdevices are known for whole blood analysis, which are based either on test stripes or on lab-on-a-chip technology. When using these devices, only a few microliters of blood are required for the blood or plasma/serum analysis. The separation of plasma/serum from whole blood is usually performed by fluid mechanical effects like the wetting behavior of different surfaces or the application of microchannels. Although this method is very attractive concerning the quick obtainment of blood analysis results, the results from these analyses are restricted to a few, test specific components. These applications are unable to replace a plasma/serum based blood analysis with the existing sophisticated systems in labs and hospitals, which comprise the analysis of a plurality of blood components and which are able to give an overall picture of a patient's state of health.

Furthermore, also for microdevices, the task of separating blood cells from the liquid part of the blood is still not solved satisfactorily.

In many countries, it is obligatory to withdraw a sufficient amount of blood from the patients to be able to store the obtained plasma/serum sample for some time to check the analysis result some time later with a so-called retain sample. Until now, the task to obtain enough cell-free plasma/serum can however only be accomplished by centrifugation.

The centrifugation procedures, which are typically used for separating blood plasma/serum from whole blood, are not only cumbersome requiring large amounts of manual and mechanical handling, but are also time consuming, which is particularly disadvantageous in emergency medicine.

Blood plasma/serum analysers, which have a great capacity for plasma/serum samples, cannot operate at full capacity, if a centrifugation process is applied upstream, which works batch-wise and represents the >>bottleneck<< in the blood sample processing. This bottleneck problem could possibly be overcome with a continuous filtration process instead of a centrifugation process for plasma/serum generation. Such a continuous system would allow a flexible analysis of the samples: Urgent samples from emergency patients could be processed with a higher priority without any need of interrupting a running centrifugation process.

It is a further advantage of a simple filtration process for whole blood separation that the whole blood separation into plasma/serum and blood cells can be performed directly after collecting the whole blood sample. This is especially advantageous for the quality of the subsequent blood analysis as the red blood cell stability decreases with increasing sample storage time. This can influence the plasma/serum composition when the plasma/serum separation is not performed immediately after the blood sample withdrawal, but with some time delay. This aspect becomes important in rural areas or developing countries when there is no centrifuge available for the plasma/serum separation and when the blood sample has to be transported for a long period of time and/or distance, sometimes even in a hot and/or humid environment.

A subsequent whole blood separation into plasma/serum can be advantageous for point-of-care testing devices, which are used to provide a quick blood analysis at/near the patient to get a quick blood analysis result outside of a clinical laboratory to make immediate decisions about patient care. Typically point-of-care testing is performed by non-laboratory personnel. A quick foregoing plasma filtration process facilitates the quick blood analysis and enables new operating conditions for point-of-care devices, since most of them work with whole blood or with the aforementioned microdevices which lead to a very small yield of plasma/serum volume. The whole blood separation process can also be integrated within the point-of-care device.

Therefore, whole blood filtration methods have been developed as an alternative measure for obtaining blood plasma/serum from whole blood. These plasma/serum filtration methods known in the art are however problematic in view of e.g. the blood cell concentration, the plasma/serum yield, the molecular absorbance capacity, the extent of hemolysis, and the leakage of blood cells (erythrocytes, thrombocytes and leukocytes). Hemolysis is one of the important problems because the red blood cells, if ruptured, will alter the concentration of some plasma/serum analytes required for further testing and, in some cases, make an analysis using optical measurements techniques impossible due to the red color of the released hemoglobin. Moreover, the leakage of blood cells is problematic because the cells or even other particles can damage the blood plasma/serum analyzers as the sensitive capillaries and conduits can become plugged. Only (substantially) cell- and hemolysis-free plasma/serum can be used for a reliable blood analysis.

Hollow fiber membrane devices permitting separation of blood plasma from whole blood without the need for a centrifugation have been used for plasma exchange therapy (PET)/apheresis. In PET, the separated plasma is eliminated and the separated blood cells with replacement fluids are returned to the patient. This hollow fiber membrane technology offers an alternative to centrifugation and conventional filtration techniques for bioseparation.

U.S. Pat. No. 5,674,394 discloses a small-volume disposable filtration technology to separate blood plasma from whole blood. The system for preparing said plasma comprises a single use filter unit having two inlets in fluid communication with each other, an outlet, and a filtration membrane selectively permeable to blood plasma separating the inlet from the outlet. Manually operable, single use pumps are connected to the inlets. A flow path is defined along the membrane between the pumps, whereby whole blood can be repeatedly exchanged between the two pumps, pass the membrane, to cause plasma to flow through the membrane and out of the outlet.

U.S. Pat. No. 5,919,356 discloses a device for sampling a fluid, preferably a body fluid such as blood, the device having filtration means for separating components of the fluid, a conduit directing flow of the fluid to be sampled from a source through the device, and sensing means which can detect the presence of a component in the fluid.

US 2003/0206828 discloses a portable hand-held blood sampling device having a self-filling capability, which includes a blood separation filter. The filter has a plurality of pores sized to permit passage of selected blood constituents such as blood plasma through the device. The filter is a hollow fiber filter, which extends within and along a length of the tube, the filter being sealed at the first end thereof proximate to the inlet end and in fluid communication with the outlet end at a second end thereof.

U.S. Pat. No. 5,906,742 A discloses a synthetic asymmetric polymeric microfiltration membrane material for separating liquids, such as blood plasma, from solids, such as blood cells. The membrane is used in wicking applications for use as testing devices.

A need remains for filter media for separating blood plasma/serum from whole blood, which allow for an effective separation of blood plasma/serum from whole blood and which are suitable for use in a quick, safe and robust way to get a suitable amount of cell-free plasma/serum, without causing hemolysis. With this kind of filtration process a deterioration of the blood quality after the blood withdrawal from the patient or bad analysis results due to a time delay in a centrifugation process or due to transportation will be avoided as the blood cell separation can be performed immediately without a centrifuge in an emergency case or at the point of collection of the blood sample.

It is therefore an object of the present invention to provide a whole blood hollow fiber membrane filter medium for separating blood plasma/serum from whole blood, which is advantageous over the prior art, in particular regarding the problems of hemolysis and leakage of blood cells (erythrocytes, thrombocytes, and leukocytes).

It is another object of the present invention to provide a whole blood hollow fiber membrane filter medium, which can be used for separating blood plasma/serum from a whole blood sample, e.g. by cross-flow filtration, wherein the separation of a sufficient amount of cell-free blood plasma/serum is possible with no or substantially no hemolysis.

Additionally, it is an object of the present invention to provide a whole blood hollow fiber membrane filter medium, which can be used for separating blood plasma/serum from a whole blood sample, wherein the material and the surface properties of the filter medium are chosen in such a manner that hemolysis due to the contact between the whole blood sample and the hollow fiber membrane filter medium is reduced or avoided. That means that negative effects like pH-shifts, osmotic changes or capillary effects caused by the porous membrane structure are reduced.

It is yet another object of the present invention to provide a whole blood hollow fiber membrane filter medium, which can be used for separating blood plasma/serum from a whole blood sample, wherein the separation of blood plasma/serum is possible, preferably in a manual way or in an easy automatic way without using centrifugation means.

It is another object of the present invention to provide a whole blood hollow fiber membrane filter medium, which can be used for separating blood plasma/serum from a whole blood sample, wherein the separation is less time consuming than the separation with conventional methods such as centrifugation methods.

It is another object of the present invention to provide a whole blood hollow fiber membrane filter medium, which can be used for separating blood plasma/serum from a whole blood sample. It should be noted in this regard that there is typically no need that the blood cells are recovered so that the whole blood hollow fiber membrane filter medium containing the blood cells can be used as a medical disposable.

It is another object of the present invention to provide a whole blood hollow fiber membrane filter medium, which can be used for separating blood plasma/serum from a whole blood sample, and which is suitable for multiple use.

It is another object of the present invention to provide a whole blood hollow fiber membrane filter medium, which can be used for separating blood plasma/serum from an urgent whole blood sample in an emergency case. Ideally, the cell separation can already take place at the scene of blood withdrawal. Subsequently the obtained plasma/serum sample can be immediately processed and can be directly delivered into the blood plasma/serum analyzer, e. g. a point-of-care testing device. The term emergency case comprises not only patient diagnosis from accidents, but also all blood treatment processes as they are provided from medical offices or patient control during surgeries in hospitals. In this regard, it is also an object to overcome the bottleneck problem of centrifugation and/or to avoid a falsification of the blood analysis due to a long treatment or transport of the unseparated whole blood sample.

It is another object of the present invention to provide a whole blood hollow fiber membrane filter medium, which can be used for separating blood plasma/serum from a whole blood sample without clogging of the filter medium.

It is another object of the present invention to provide a whole blood hollow fiber membrane filter medium, which can be used for separating blood plasma/serum from a whole blood sample, wherein the whole blood hollow fiber membrane filter medium does not induce rupture of blood cells e.g due to frictional forces or other mechanical stresses.

It is another object of the present invention to provide a whole blood hollow fiber membrane filter medium, which can be used for separating blood plasma/serum from a whole blood sample, and reduces the risk of a leakage of red blood cells into the filtrate.

It is another object of the present invention to provide a whole blood hollow fiber membrane filter medium, which is suitable for providing a blood cell containing concentrate with which further testing is possible if desired.

It is another object of the present invention to provide a whole blood hollow fiber membrane filter medium, which leads to a cell-free or substantially cell-free plasma/serum as a filtrate wherein the relative amounts of the molecular components to be analyzed remain substantially unchanged upon filtration. Ideally, the whole blood hollow fiber membrane filter medium is inert and hemocompatible, releases no extractables or particles, and neither leads to the adsorption of particular blood plasma/serum components on its solid surface nor to a cross-reaction of particular blood plasma/serum components with its solid surface.

SUMMARY OF THE INVENTION

The above mentioned objects of the present invention are achieved by a whole blood hollow fiber membrane filter medium including a polymeric material having a pore size ensuring permeability to blood plasma or serum, but retaining blood cells, i.e. all three kinds of blood cells (erythrocytes, thrombocytes and leukocytes). In order to allow subsequent blood plasma/serum analysis, the pore size ensures permeability to all molecular plasma/serum components. Plasma/serum components can be classified into different groups including electrolytes, lipid metabolism substances, markers, e.g. for infections or tumors, enzymes, substrates, proteins and even pharmaceuticals and vitamins.

The pore structure may be defined e.g. by the median and average diameter of the pores, the pore size distribution, and the porosity of a material. Preferably, the properties of the whole blood hollow fiber membrane filter medium regarding the average diameter of the pores, the pore size distribution, and the porosity are selected in such a way that the filter medium is suitable for avoiding hemolysis and leakage of blood cells. Furthermore, the surface roughness of the whole blood hollow fiber membrane filter medium is preferably selected in such way that the blood cells are not ruptured by frictional forces. Moreover, it can be preferred that the whole blood hollow fiber membrane filter medium is modified in that it is e.g. pre-wetted or coated in order to obtain certain wettability properties, hydrophilic/hydrophobic properties, oleophilic/oleophobic properties or a certain surface charge of the filter medium, which can be advantageous in terms of avoiding hemolysis and the leakage of blood cells.

The objects of the present invention are also achieved by the use of the whole blood hollow fiber membrane filter medium of the invention for separating blood plasma/serum from a whole blood sample. Preferably, the whole blood hollow fiber membrane filter medium of the invention is used for separating blood plasma/serum from a whole blood sample by cross-flow filtration to avoid clogging of the filter medium.

DESCRIPTION OF PREFERRED EMBODIMENTS

Figure 1:
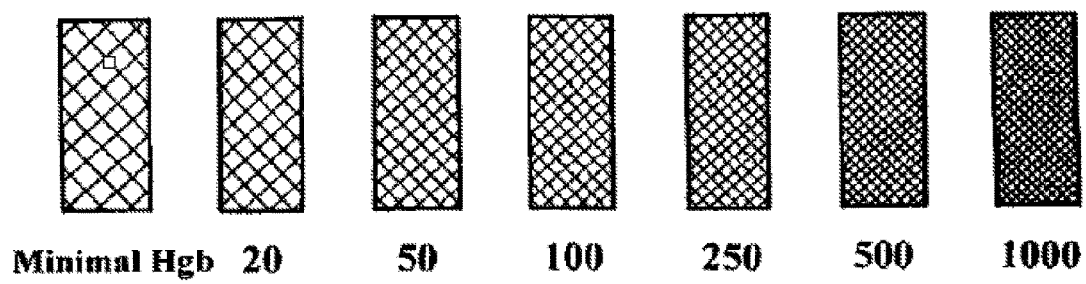
FIG. 1 shows reference solutions including different amounts of hemoglobin for determining the degree of hemolysis in blood plasma samples (see Jie Zhao, Quancheng Kan, Jianguo Wen, Yidong Li, Yunqiao Sheng, Li Yang, Jason Wu and Shengjun Zhang: *Hemolysis of Blood Samples has no Significant Impact on the Results of Pharmacokinetic Data. Bioequivalence & Bioavailability,* 2012).

As used herein, the term "whole blood" refers to blood composed of blood plasma, which is typically unclotted, and cellular components. The plasma represents about 50% to about 60% of the volume, and cellular components, i.e. erythrocytes (red blood cells, or RBCs), leucocytes (white blood cells, or WBCs), and thrombocytes (platelets), represent about 40% to about 50% of the volume. As used herein, the term "whole blood" may refer to whole blood of an animal, but preferably refers to whole blood of a human subject.

Erythrocytes constitute about 90% to about 99% of the total number of all blood cells and have the form of biconcave discs and measure about 7 µm in diameter with a thickness of about 2 µm in an undeformed state. During maturation in the bone marrow, the erythrocytes lose their nucleus. They contain the plasma membrane protein spectrin and other proteins to provide flexibility to change shape as necessary. Their unique and flexible shape enables them to pass through very narrow capillaries and provides for maximum surface area to transfer oxygen and carbon dioxide. This flexibility makes it particularly difficult to separate the red blood cells from a whole blood sample by filtration as they can elongate themselves and reduce their diameter down to about 1.5 µm. Normal whole blood has approximately 4.5 to 5.5 million erythrocytes per microliter. The life-span of erythrocytes is approximately 120 days in the circulating bloodstream. One core component of erythrocytes is hemoglobin which binds oxygen for transport to the tissues, then releases oxygen and binds carbon dioxide to be delivered to the lungs as waste product. Hemoglobin is responsible for the red color of the erythrocytes and therefore of the blood in total. Erythrocytes are the major factor contributing to blood viscosity.

Leucocytes make up less than about 1% of the total number of all blood cells and can be differentiated into different white blood cell groups (lymphocytes, granulocytes, and monocytes). They can leave capillaries via diapedesis. Furthermore, they can move through tissue spaces by amoeboid motion and positive chemotaxis. They have a diameter of about 6 µm to about 20 µm. Leucocytes participate in the body's defense mechanisms e.g. against bacterial or viral invasion.

Thrombocytes are the smallest blood cells with a length of about 2 µm to about 4 µm and a thickness of about 0.9 µm to about 1.3 µm. They are membrane-bound cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50 vol.-% to about 60 vol.-%). Plasma is devoid of cells, and unlike serum, has not clotted. So it contains all coagulation factors, in particular fibrinogen. It is a clear yellowish liquid including about 90 vol.-% to about 95 vol.-% water.

The term "blood serum" or "serum" refers to the clear liquid that separates from blood when it is allowed to clot completely, and is therefore blood plasma from which in particular fibrinogen has been removed during clotting. Like plasma, serum is light yellow in color.

Molecular plasma/serum components can be classified into different groups including electrolytes, lipid metabolism substances, markers, e.g. for infections or tumors, enzymes, substrates, proteins and even pharmaceuticals and vitamins.

As used herein, the term "cell-free" describes a plasma/serum sample with no or substantially no cells (erythrocytes, leucocytes, thrombocytes) in its volume that is prepared by e.g. a centrifuge. A substantially cell-free or cell-free sample is needed for a subsequent plasma/serum analysis to prevent blocking of the analysis system.

For the plasma analysis performed with the plasma, which is obtained by filtration, the following analytes may be chosen which comprise the relevant molecular groups. The reference concentration ranges of these chosen analytes for whole blood with heparin stabilization depend on the applied measurement technique. The following exemplary reference concentration ranges of these chosen analytes are obtained by the analysis device "Dimension" from Siemens.

| Plasma components | | Reference concentration ranges of analytes for whole blood with heparin stabilization and the chosen measurement device |
|---|---|---|
| Electrolytes | Potassium | 3.5-5.1 mmol/l |
| | Sodium | 136-145 mmol/l |
| | Calcium | 2.12-2.52 mmol/l |
| | Magnesium | 0.74-0.99 mmol/l |
| | Chloride | 98-107 mmol/l |
| | Phosphate | 0.80-1.60 mmol/l |
| Lipids | Triglycerides | 75-175 mg/dl |
| | Cholesterol | 110-200 mg/dl |
| | HDL-cholesterol | 35-60 mg/dl |
| | LDL-cholesterol | <150 mg/dl |
| Infection markers | CRP | 0-5.00 mg/l |
| Enzymes | AST/GOT | 0-35 Unit/l |
| | Lipase | 114-286 Unit/l |
| Substrates | Albumin | 3.4-5.0 g/dl |
| | Bilirubin | 0-1.0 mg/dl |
| | Glucose | 74-106 mg/dl |
| | Creatinine | 0.60-1.30 mg/dl |
| Proteins | IgG | 6.81-16.48 g/l |
| | Ferritine | 3.0-244 ng/l |

The analysis device "Dimension" from Siemens may not only be used for the analysis of blood plasma, but also for the analysis of blood serum.

As used herein, the expression "ensuring permeability to blood plasma or serum" preferably means that none of the above mentioned plasma or serum components to be analyzed is retained completely upon filtration. Preferably, the concentrations of the plasma or serum components to be analyzed are not significantly changed compared to the whole blood sample upon filtration. More preferably, the concentrations of the plasma or serum components to be analyzed are changed by not more than about 50%, preferably by not more than about 35%, more preferably by not more than about 10%, most preferably by not more than about 8%.

As used herein, the term "hemolysis" refers to the rupture of erythrocytes, e.g. due to chemical, thermal or mechanical influences, causing the release of the hemoglobin and other internal components into the surrounding fluid. Hemolysis can be visually detected by showing a pink to red tinge in the plasma/serum. Hemolysis is a common occurrence seen in serum and plasma samples and may compromise the laboratory's test parameters for blood analysis. Hemolysis can originate from two sources. In vivo hemolysis may be due to pathological conditions such as autoimmune hemolytic anemia or transfusion reaction. In vitro hemolysis may be due to improper specimen sample collection, specimen sample processing or specimen sample transport. In particular, hemolysis may be caused by a high pressure drop and high shear or elongation rate, which may e.g. occur during filtration processes, when the sample is passed through a porous filter medium. Other important factors for hemolysis are bacterial contamination, pressure, temperature, osmotic environment, pH value, contact with surfaces, frictional forces, blood age and storage time of the unseparated whole blood sample.

The degree of hemolysis can be detected visually in comparison to a plasma reference solution having a certain concentration of hemoglobin (Hb, Hgb) (see e.g. FIG. 1). Blood plasma samples having the same color as a reference solution including no hemoglobin show no hemolysis. Blood plasma samples being equally or less red than a solution including about 50 mg/dl hemoglobin show substantially no hemolysis. In this respect, "substantially no hemolysis" means that the blood plasma samples show such a degree of hemolysis that is still sufficiently low to ensure that the samples can be analyzed with satisfactory results, e.g. by the plasma analysis device "Dimension" from Siemens. Blood plasma samples being equally or less red than a solution including about 100 mg/dl hemoglobin show a medium degree of hemolysis. Blood plasma samples with a color corresponding to a solution with a higher hemoglobin content than 100 mg/dl show a high degree of hemolysis. Reference solutions including 20, 50, 100, 250, 300 and 1,000 mg/dl are provided in FIG. 1.

For the filtration of whole blood, there are in principle different filtration processes available. Based on process technology, filtration processes are subdivided into three different operational modes
Dead-end filtration as a static operational mode
Cross-flow filtration as a dynamic operational mode
Submerged filtration systems In the dead-end operational mode, the feed flux is typically orthogonal to the surface of the hollow fiber membrane filter medium and the hollow fiber membrane filter medium is flowed through typically orthogonally by the filtrate so a dead-end module is operated as a two-end module. All particles to be retained are deposited on the membrane surface. The so-called cover layer leads to a time-dependent, increasing flow resistance and the permeate flux through the membrane is reduced over time, typically in a constant pressure operational mode. After a certain filtration time-interval, the module has to be flushed to remove the cover layer. Typically, dead-end filtration is a discontinuous process.

In the cross-flow filtration mode, there is typically a flux parallel to the surface of the hollow fiber membrane filter medium on the feed side. Also in the cross-flow mode, the particles to be separated are deposited on the membrane surface and build up a cover layer. With the feed flux parallel to the cover layer, there is a control mechanism for the cover layer formation. Cross-flow shear forces are induced at the membrane surface, which can transport deposited particles from the cover layer to the feed flux. The cover layer can become steady state, if there is a balance between particle deposition and particle re-entrainment. If the pressure drop of the cover layer increases, a constant or pulsating back-flushing with the filtration permeate is applied to remove the cover layer.

Thus, the term "cross-flow filtration" as used herein refers to a filtration process, wherein a feed stream tangentially passes across the surface of a hollow fiber membrane filter medium or another type of filter medium, and two exiting streams are generated. The permeate or filtrate stream is the portion of the fluid that passes through the filter medium. This permeate or filtrate should contain the same percentage of soluble and/or insoluble components as the initial feed stream, provided these components are smaller than the pore size of the filter medium. The retentate stream is the remainder of the feed stream, which does not pass through the filter medium, but may continue to flow across the filter medium, thereby "cleaning" and thickening. This "cleaning" is to be understood in that the use of a tangential flow will prevent thicker particles from clogging the membrane as observed for example in filter cakes in dead-end filtration processes. The filtrate volume can be increased by repeatedly passing the retentate across the filter medium. Besides the pulsating flow from one side of the filter housing to the other, a circuit operation mode is, in principal, also possible.

In principal, "cross-flow filtration" is highly advantageous for the purpose of the present invention, i.e. whole blood filtration, because it is particularly suitable for the pressure and shear force sensitive blood cells. Especially erythrocytes are very sensitive concerning static pressure drop which leads to cell deformation. The application of a cross-flow current along a membrane keeps the cells in movement within the liquid phase and away from the membrane surface so that it is possible to perform the filtration with an elevated transmembrane pressure at a simultaneously reduced risk of hemolysis because a high transmembrane pressure as well as plugging of the filter medium due to a high cell amount can effectively be avoided. To gain the plasma/serum for further analysis or storage, the whole blood samples to be filtered by means of cross-flow filtration typically have a volume of from about 0.01 ml to about 10 ml.

As used herein, "outside-in" or "out-in" cross-flow filtration describes an operating mode of filter media of tubular or capillary shape, e.g. hollow fiber membrane filter media. In this operating mode, the feed stream flows outside and between the filter medium in the shell side of the filter module and the filtrate penetrates through the filter medium wall to the inside. The retention typically takes place at the outer surface of the filter medium and sometimes to a low degree within the filter medium itself.

Figure 2:
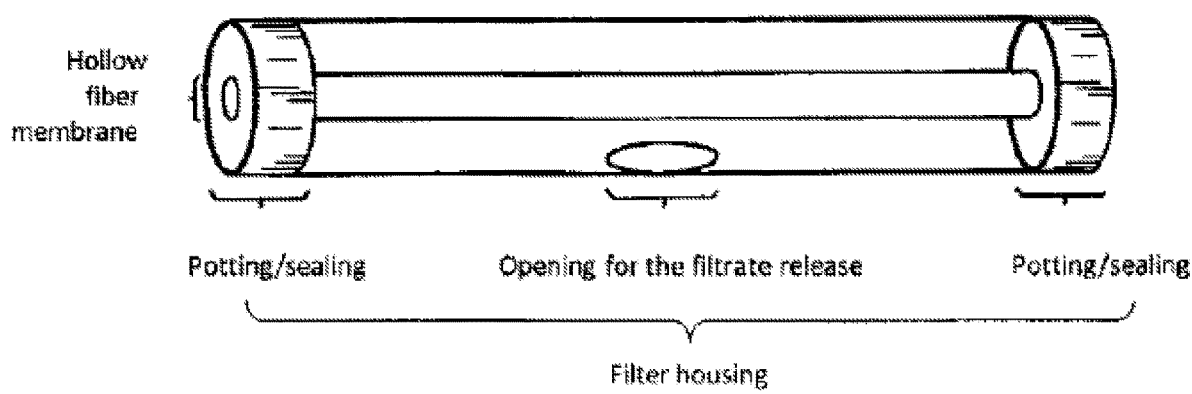
FIG. 2 shows a cross-flow filtration module including a single whole blood hollow fiber membrane filter medium inside a filter housing.

As used herein, "inside-out" or "in-out" cross-flow filtration describes the opposite operating mode of the hollow fiber membrane filter medium compared to the "out-in" operating mode. The feed flows inside the filter medium and the filtrate penetrates through the filter medium wall to the outside. The retention typically takes place at the inner surface of the tubular filter medium and sometimes to a low degree within the filter medium itself. An exemplary in-out cross-flow filtration module is shown in FIG. 2.

The out-in configuration provides more flexibility in the amount of feed to flow around the hollow fiber membrane filter medium, whereas the in-out configuration offers a much more defined and homogeneous flow distribution through the bore of the hollow fiber membrane filter medium compared to the out-in configuration. The in-out arrangement is close to a bionic principle: Blood flow in narrow capillaries tends to produce an almost cell-free boundary plasma layer adjacent to the vessel wall as the blood cells arrange themselves in the middle of the blood flow where the flow velocity is highest. It is believed that this cell distribution facilitates the filtration as this cell distribution reduces the risk of pore plugging and subsequent hemolysis.

As used herein, the term "hollow fiber membrane filter medium" refers to a membrane filter medium preferably of tubular or capillary shape, which is preferably suitable for use in cross-flow filtration, more preferably for use in the in-out filtration mode. Dead-end filtration is also possible with an in-out filtration mode. Cross-flow filtration is preferred according to the present invention, however. Similarly, with an out-in filtration mode, cross-flow and dead-end filtration are also possible, wherein cross-flow filtration is also preferred. Such hollow fiber membrane filter media may be prepared by a technique referred to as phase inversion. Phase inversion can be achieved by solvent evaporation, non-solvent precipitation and thermal gelation. In principal, phase separation processes can e.g. be applied to a large number of polymers but also to glasses, ceramic materials and metal alloys.

Polymeric hollow fiber membrane filter media can principally be prepared by a phase inversion process as described in the following.

A viscous spinning dope including at least one polymer and at least one solvent and optionally at least one additive e.g. for viscosity adjustment or membrane pore stabilization is prepared by stirring. The polymer (polymeric granulate material) is soluble in the solvent. Preferred polymers in this regard are e.g. polyacrylonitrile, polypropylene, polyamide, polysulfone, polyvinyldifluoride or polyethersulfone, more preferred are polyacrylonitrile, polypropylene, polyamide, polyvinyldifluoride or polyethersulfone, and most preferred are polyethersulfone and polypropylene; a preferred solvent is e.g. n-methyl-pyrrolidone. The amount of the polymer based on the total weight of the spinning dope is from about 1 weight % to about 50 weight %, the amount of the solvent based on the total weight of the spinning dope is from about 10 weight % to about 90 weight %. Typically, additive components are homogenized with the spinning dope, e.g. additives for viscosity adjustment or membrane pore stabilization and others. These additive components are typically used in amounts of up to about 50 weight % based on the total weight of the spinning dope.

After homogenization, the spinning dope is degassed and conducted through the annulus cross-section of a multi-component nozzle, giving the hollow fiber structure to the polymeric hollow fiber membrane filter material. The bore fluid is conducted through the nozzle through the bore volume along the nozzle axis. The spinning velocity of the spinning dope is preferably from about 0.5 m/min to about 50 m/min. The fluid velocity of the bore fluid is preferably from about 0.06 m/min to about 60 m/min. This refers to volume flow rates of typically from about 0.01 liters/h to about 5 liters/h for the spinning dope and typically from about 0.007 liters/h to about 2.8 liters/h for the bore fluid. The spinning process is performed within an ambient temperature range from about 10° C. to about 40° C., preferably from about 18° C. to about 35° C. The overpressure imposed on the spinning dope in front of the spinning nozzle is preferably lower than 10 bar. In a more preferable operation mode, it is lower than 6 bar.

When the spinning dope contacts the solvent-free, typically aqueous precipitation bath and the bore fluid at the nozzle orifice, the solvent within the spinning dope is removed by water and the spinning dope solidifies (phase inversion) as the polymer is not soluble in the precipitation bath. Typically, the bore fluid has the same composition as the precipitation bath fluid into which the spinning dope is guided. By the contact of the spinning dope with the bore fluid and the precipitation bath, an inner and an outer precipitation process are initiated at the inner and the outer surface of the hollow fiber. Dependent on the solvent content of the precipitation bath and the bore fluid and dependent on additives, the temperature and the viscosity of the precipitation bath and the bore fluid, the diffusion process, which controls the formation of the porous membrane structure during precipitation, is influenced. With a high diffusion velocity, a finger pore structure is generated, with low diffusion velocities, a sponge membrane structure is generated.

The composition of the precipitation bath and the bore fluid can be similar or different. With a similar composition of both fluids, similar diffusion velocities result at the outside and at the inside of the polymeric hollow fiber membrane filter medium during the precipitation process and the polymeric hollow fiber membrane filter medium shows an almost symmetrical pore structure. With a different composition of both fluids, different diffusion velocities result at the outside and the inside of the polymeric hollow fiber membrane filter medium during the precipitation process and the polymeric hollow fiber membrane filter medium shows an asymmetric pore structure, preferably with a gradient in the pore size distribution and the porosity across the wall of the polymeric hollow fiber membrane filter medium.

The spinning dope is usually directly guided into the precipitation bath when the orifice of the spinning nozzle is dipped into the precipitation bath. In another preferred spinning process design an air gap with a maximum length of 40 cm is adjusted between the orifice of the spinning nozzle and the surface of the precipitation bath. Preferably, the water used in the precipitation bath and in the bore fluid is ion-free water that is produced by reverse osmosis in order to prevent plasma/serum falsification of the permeate during filtration by ions retained from the hollow fiber membrane filter medium production.

The solidified polymer defines the hollow fiber membrane filter medium structure. The resulting fiber is deposited within the precipitation bath and solvent molecules are washed out. Preferably, the hollow fiber membrane filter media are treated in one or more subsequent washing baths to remove remaining solvent molecules. The resulting fiber is then laid in liquid conditioning material for filling up the pores and preventing the pores from collapsing in the next step. Then the fiber is dried at a temperature of from about 15° C. to about 40° C. for a time interval of from about 10 hour to about 48 hours. This process produces a single layer polymeric hollow fiber membrane filter medium which can be subjected to further surface modification, e.g. by coating or by pre-treating, e.g. pre-wetting, it.

The basic concept of this process as well as the physical and technical principles for the generation of hollow fiber filter media are described in the granted patent DE 199 10 012 C1. Some basic differences between the present process of the inventors and the process as described in the patent DE 199 10 012 C1 arise. The patent DE 199 10 012 C1 describes a process in which two polymer solutions are used to produce a multi-layer material, whereas in the process of the inventors only one polymer solution is used to produce a single-layer hollow fiber membrane filter medium. Furthermore, the patent DE 199 10 012 C1 describes a process in which polysaccharides, derivatives of polysaccharides or polyvinyl alcohol are used as polymers, whereas in the process of the inventors e.g. polyacrylonitrile or polyethersulfone is used. Furthermore, the patent DE 199 10 012 C1 describes a process in which amine-n-oxide is used as a solvent, whereas in the process of the inventors e.g. n-methyl-pyrrolidone is used as a solvent for the preparation of the spinning dope.

The production of hollow fiber membrane filter media by phase inversion is also described in the patent application DE 101 48 768 A1 filed by the present applicant.

After their preparation, the polymeric hollow fiber membrane filter media should be handled with gloves to prevent contamination with the lipids of skin.

In another preferred embodiment, the polymeric whole blood hollow fiber membrane filter medium can be manufactured by an extrusion process instead of the above mentioned spinning process. In this extrusion process, the spinning dope is pressed through a hole plate to generate the geometrical shape of the polymeric hollow fiber membrane filter medium and guided into an aqueous precipitation bath where the spinning dope solidifies.

In another preferred embodiment, the polymeric whole blood hollow fiber membrane filter medium can be manufactured by a sintering process instead of the above mentioned spinning or extrusion processes. In this sintering process, a polymeric powder is introduced into a shape defining tool and compressed at an operation temperature which is lower than the melting temperature.

As used herein, the term "polymeric material" refers to an organic material, which belongs to thermoplastic materials, e.g. polyacrylonitrile, polypropylene, polyamide, polysulfone, polyvinyldifluoride or polyethersulfone, preferably polyacrylonitrile, polypropylene, polyamide, polyvinyldifluoride or polyethersulfone, and more preferably polyethersulfone or polypropylene.

For hollow fiber membrane filter media, the pore size is an important characteristic for achieving a desired separation of components from a sample, such as the separation of blood plasma/serum from a whole blood sample. The pore size may be defined by the size of the molecules which are retained (molecular weight cut-off, MWCO). Alternatively, the pore size may be defined by the number-related or volume-related average diameter or mean flow diameter of the pores, preferably by the mean flow diameter of the pores. Another important parameter in this regard is the volumetric pore size distribution (pore size distribution). Still further, other measures to describe the pore structure, such as the accessible porosity may be used.

The MWCO is defined as the molecular weight solute (in Daltons, Da) in which 90%, preferably 95%, more preferably 99%, of the solute is retained by the membrane, or the molecular weight of the molecule (e.g. globular protein) that is retained to 90%, preferably 95%, more preferably 99%, by the membrane.

The pore size parameters can be determined by capillary flow porometry. Capillary flow porometry is based on the displacement of a wetting liquid inside a porous network by means of an inert gas flow. The wetting liquid spontaneously enters the pores in a material as a result of the capillary force until the height of liquid equilibrates with the gravity. Different parameters determine the height obtained by the liquid inside this capillary opening: the diameter of the opening, the air pressure, the interphase interaction between the liquid and solid, the density of the liquid, the viscosity and the temperature, among others. It is known that the Young-Laplace equation establishes the relationship between the pressure across an interface between two fluids (in this case the wetting liquid and the air) and the diameter of the capillary which is filled by the two fluids including the interface. The formula that relates these two variables is:

$$\text{Pressure} = 4 \ast \gamma \ast \cos\theta \ast (\text{shape factor})/\text{diameter of the capillary}$$

wherein $\gamma$ is the surface tension of the wetting liquid, $\theta$ the contact angle of the liquid on the solid. The shape factor is a parameter depending on the shape and the path of the pore inside the material.

The surface tension $\gamma$ is a measurable physical property and is available for many liquids. The contact angle $\theta$ however depends on the interaction between the material and the wetting liquid. Typical wetting fluids used in porometry are perfluoroethers. They have a low surface tension and a contact angle of 0° with nearly all materials.

A capillary flow porometer consists of one or more pressure and flow sensors with a separate pressure control. The instrument will build up pressure inside the pressure chamber starting from ambient pressure, over a wetted sample. Gradually, the pores will start to open starting with the largest pores and a gas flow will be measured. The pressure buildup is performed until all pores are opened and the sample has completely dried during this so-called wet curve. The instrument deflates and a second run is performed, called the dry curve. This curve is necessary for the calculation of all measured parameters: largest and smallest pores, mean flow pore size, and so on.

The pressure may be increased by the pressure control in two differentiated ways. A first one is the linear increase of pressure over time with immediate data sampling for pressure and flow. This pressure scan methodology can be performed e.g. in a POROLUX™ 100 series instrument available from the manufacturer >>Porometer<<. In POROLUX™ 1000 series instruments, the pressure is increased in different steps. At each pressure step, both pressure and flow are monitored and a datapoint is taken when stabilization criteria are met. This pressure step/stability method provides more accurate information and can also be used at increased pressures. The methods also allow to determine the first bubble point with the calculated bubble point and/or the "true" measured bubble point method.

All measurements performed in a capillary flow porometer consist of two gas flow curves as a function of (relative) pressure increase. The instrument itself will calculate from these two curves all important parameters. Typical parameters are: first bubble point or largest pore, mean flow pore, smallest pore, cumulative flow, differential flow and corrected differential flow.

Figure 3:
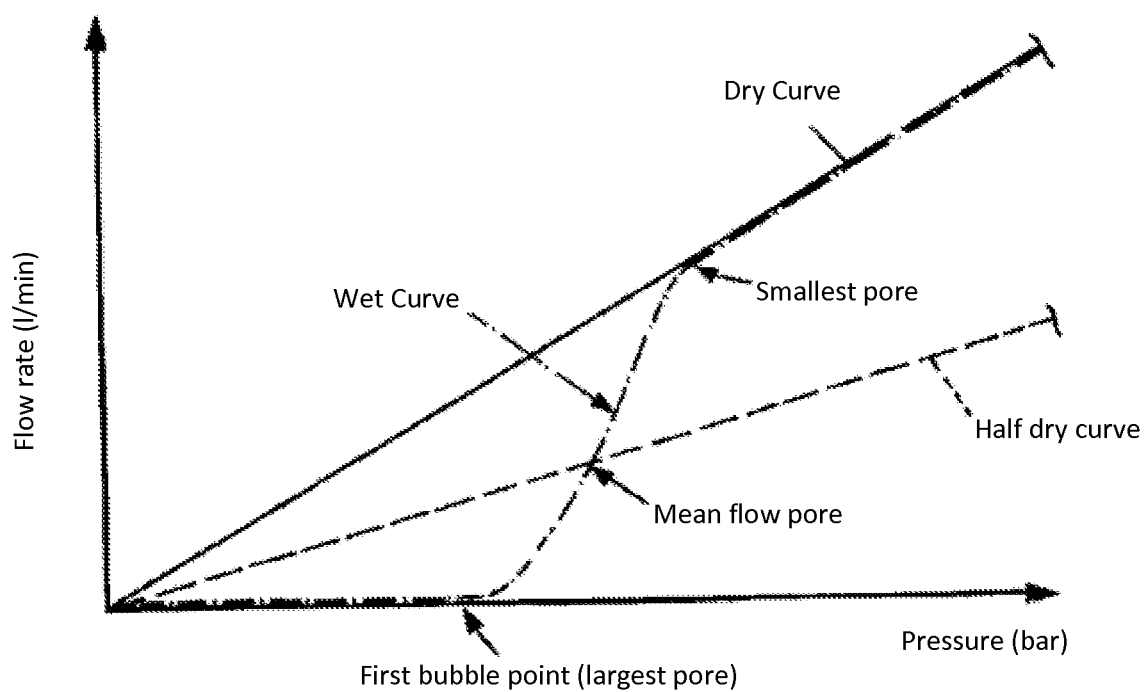
FIG. 3 shows measurement of pore parameters in a capillary flow porometer.

Typical curves from which the parameters can be calculated are depicted in FIG. 3. The first bubble point defines the largest pores present inside the material. ASTM F-316-03 defines the first bubble point as the pressure at which the first continuous gas bubbles are detected. The smallest pore represents the smallest openings inside the material. These are opened right before the filter has completely dried. The smallest pores are therefore calculated at the point where the wet curve and dry curve start to coincide. The average pore size or mean flow pore size is calculated at the pressure where the wet curve and the "half-dry" curve cross. The half-dry curve is obtained by the mathematical division by 2 of the data originating from the dry curve, as requested by the standard ASTM F 316-03.

Figure 4:
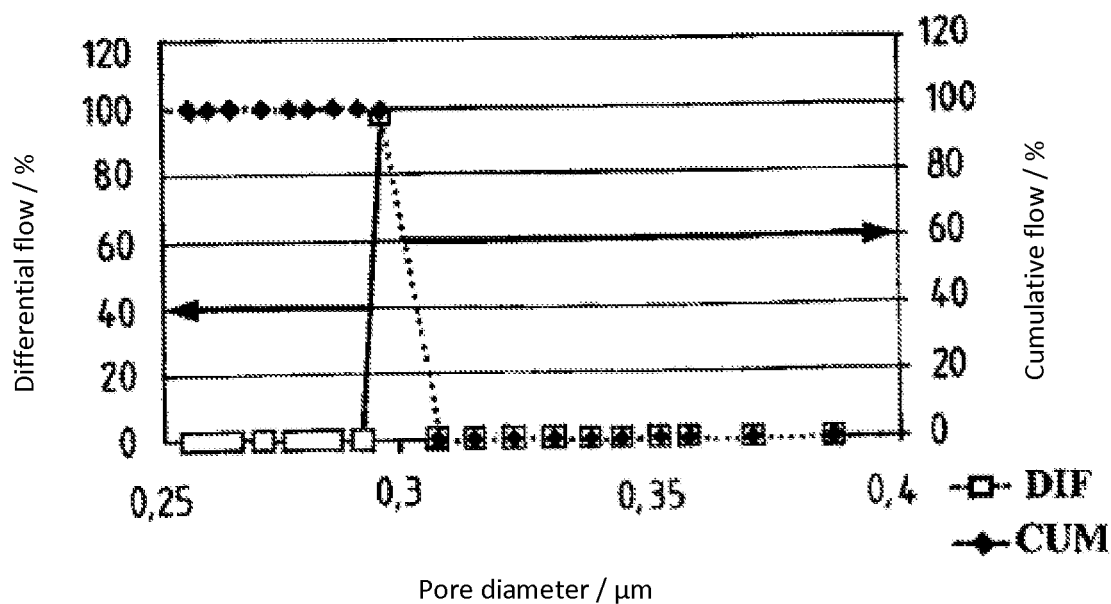
FIG. 4 shows differential and cumulative flow curves obtainable with a capillary flow porometer.

From the wet and dry curves also the pore size distribution is calculated, shown with the cumulative, differential and corrected differential flow, see the FIG. 4. The differential flow shows the percentage of pores present. The cumulative flow represents the sum of all these differential values between 0 and 100%. The corrected differential takes also the differences in pore size relative to its pressure step into account.

The median pore diameter and the pore size distribution can be determined by mercury intrusion porosimetry. In mercury intrusion porosimetry, gas is evacuated from the sample cell, and mercury is then transferred into the sample cell under vacuum and pressure is applied to force mercury into the sample. During measurement, applied pressure (p) and intruded volume of mercury (V) are registered. As a result of analysis, an intrusion-extrusion curve is obtained. Parameters describing the pore structure of the sample can be calculated from the data obtained. The principle of this technique is based on the fact that mercury does not wet most substances and, therefore, will not penetrate pores by capillary action, unless it is forced to do so. Liquid mercury has a high surface tension ($\gamma$) and also exhibits a high contact angle ($\theta$) against most solids. Entry into pore spaces requires applying pressure (p) in inverse proportion to the pore radius (r). Based on these known parameters, the pore radius can be determined by the Washburn equation (Washburn 1921):

$$p \times r = -2 \times \gamma \times \cos\theta$$

wherein r is the radius of the pore where mercury intrudes, $\gamma$ is the surface tension of mercury, and $\theta$ is the contact angle of the mercury on the surface of a solid sample.

Generally used values for the surface tension and the contact angle of mercury are 480 mNm$^{-1}$ and 140°, respectively. According to the Washburn equation, the radius of the pores can therefore be calculated from the applied pressure.

The measurements for the mercury intrusion porosimetry are performed according to DIN 66133.

The total pore volume ($V_{tot}$) is the total intruded volume of mercury at the highest pressure determined. The total pore surface area (S), which is also often referred to as specific pore surface area, is calculated by the following equation:

$$S = \frac{1}{\gamma|\cos\theta|} \int_0^{V_{tot}} p\, dV$$

The total pore surface area (S) is the area above the intrusion curve.

The mean pore diameter ($d_{mean}$), which is also often referred to as average pore diameter or hydraulic diameter, is calculated by the following equation $$d_{mean} = 4 \cdot \frac{V_{tot}}{S}$$

based on an assumption of cylindrical shape of pores open at ends.

The median pore diameter ($d_{median}$) is the pore diameter at which 50% of the total intruded volume of mercury is intruded into the sample. In general, the mean pore diameter emphasizes the smaller pores rather more than the median pore diameter.

The volumetric pore size distribution curve is characterized by three values of the cumulative residue curve: D10 (10% of the pore volume consists of pores with a bigger diameter than D10), D50 (median pore diameter $d_{median}$, 50% of the pore volume consists of pores with a bigger diameter than D50) and D90 (90% of the pore volume consists of pores with a bigger diameter than D90). The closer the values for D10 and D90 are to each other, the narrower is the pore size distribution, indicated by a value for the ratio of D10/D90, which is close to 1.

In addition, mercury intrusion porosimetry can provide the accessible porosity of a material. Porosity is a measure of the void (i.e. "empty") spaces in a material, and is a fraction of the volume of voids over the total volume, between 0-1, or as a percentage between 0-100%. Accessible porosity refers to the fraction of the total volume, in which fluid flow is effectively taking place, and includes open pores, in particular dead end pores, but excludes closed pores.

Fully automated mercury porosimeters for the determination of volume pore size distribution, median pore diameter, total pore volume and specific pore surface are commercially available e.g. from Porotec GmbH. Different instruments and options allow the possibility to determine pore radii from 3,000 microns to 1.8 nm.

Furthermore, it is advantageous in terms of the prevention of hemolysis when the surface of the hydrophilic hollow fiber membrane filter medium has a reduced wettability because capillary effects during the first contact with blood can be reduced and the flux during the filtration process can also be reduced. A reduced wettability can e.g. be achieved by applying a coating, which has a reduced hydrophilicity. Without being bound to theory, it is assumed that a "low" wettability is highly advantageous for whole blood filtration. In this regard, "low" wettability means that a water or blood droplet should have a contact angle of about 60°-90°, preferably of about 80°-89.9°, ro a planar reference surface made of borosilicate glass which was treated with the same chemical coating agents. In this case the wettability is reduced compared to a uncoated hydrophilic surface, but the coated surface is still hydrophilic according to the following definition: Hydrophilic surfaces lead to a water or blood droplet contact angle smaller than 90°, hydrophobic surfaces lead to a water or blood droplet contact angle bigger than 90°. Thus, the term "low" wettability preferably does not cover hydrophobicity of the surface. For the case of hydrophobic surface properties of a membrane, a higher transmembrane pressure would be necessary which would lead to slower and lower plasma recovery and/or to a damage of blood cells and therefore to hemolysis.

The wettability can be determined e.g. on coated glass slides: The contact angle of water on an uncoated and hydrophilic glass surface is about 44°, the contact angle of water on coated glass can be about 60°-90° depending on the coating process and the water droplet size.

In another preferred embodiment, a reduced wettability can also be achieved by using less hydrophilic membrane materials or by graft copolymerization.

Any medium or material which shows no interaction with whole blood is generally described as "hemocompatible". No interaction means especially that the medium or material does not cause blood clotting, e.g. by interacting with the blood coagulation system or the blood platelets. Accordingly, a hemocompatible material has no thrombotic effect. It is preferred that the hollow fiber membrane filter media according to the present invention are hemocompatible. Furthermore, it is preferred that the filter media do not modify any blood component concentrations by adsorption or reaction and that the contact with whole blood does not cause hemolysis.

In a first embodiment, the present invention is directed to a whole blood hollow fiber membrane filter medium including a polymeric material having a pore size ensuring permeability to blood plasma or serum, but retaining blood cells. Preferably, the whole blood hollow fiber membrane filter medium consists of a polymeric material having a pore size ensuring permeability to blood plasma, but retaining blood cells.

In a preferred embodiment, the present invention is directed to a whole blood hollow fiber membrane filter medium including a polymeric material having a pore size ensuring permeability to blood plasma.

In a preferred embodiment, the pore size of the whole blood hollow fiber membrane filter medium of the invention ensures permeability to all components of blood plasma/serum, in particular to electrolytes, lipid metabolism substances, markers, e.g. for infections or tumors, enzymes, substrates, proteins and even pharmaceuticals and vitamins. Accordingly, it can be ensured that a subsequent analysis of the blood plasma/serum is based on an unchanged molecular composition of the respective components and, accordingly, an adequate determination of the required analytes is possible.

In a preferred embodiment, the whole blood hollow fiber membrane filter medium is a whole blood hollow fiber membrane cross-flow filter medium. It can either be used for out-in or for in-out cross-flow filtration. In-out cross-flow filtration is preferred due to the advantages of the cell distribution inside of the above mentioned flow conditions. Amounts of whole blood, which can be filtered with the whole blood hollow fiber membrane filter medium of the invention, are preferably in the range of from about 0.01 ml to about 10 ml, more preferably from about 0.1 ml to about 5 ml, most preferably from about 0.5 ml to about 3 ml. Preferably at least about 0.005 ml blood plasma/serum, more preferably at least about 0.05 ml, most preferably at least about 0.25 ml blood plasma/serum can be obtained from the above amounts of whole blood.

In order to allow for cross-flow filtration, preferably in-out cross-flow filtration, the whole blood hollow fiber membrane filter medium of the invention is preferably open at both ends. At these ends, the whole blood hollow fiber membrane filter is preferably connected to pumping devices to impose the differential pressure which is required for the flux and for the filtration process. Preferably, the whole blood hollow fiber membrane filter medium is surrounded by a tubular housing, which has an opening for the filtrate release, if it is used in an in-out cross-flow filtration process.

With the above mentioned pumping devices, several blood passes of the whole blood through the filter module can be performed. Preferably, about 1 to about 80 blood passes are realized, more preferably about 10 to about 40 blood passes are realized. Within each blood pass a certain amount of plasma/serum is removed from the whole blood passing through the porous filter medium and the whole blood as the feed fluid is thickened due to the increasing blood cell concentration. The number of blood passes depends on the cell concentration of the whole blood sample, the age of the whole blood sample, the patient's state of health, the number of hollow fiber membranes within the filter module, the fiber properties, the filtration velocity, the system pressure and the required volume of the separated plasma/serum. The overpressure inside of the filter module should be at most about 1.5 bar, preferably at most about 1.2 bar, most preferably about 1.0 bar compared to the ambient pressure. The overpressure is imposed to overcome the transmembrane pressure drop and the pressure drop of the macroscopic flux through the hollow fiber bore channel.

In another preferred embodiment, the whole blood hollow fiber membrane filter medium is a whole blood hollow fiber membrane dead-end filter medium.

In another preferred embodiment, the whole blood hollow fiber membrane filter medium of the invention allows molecules of less than about 8,000 kDa, preferably less than about 10,000 kDa, more preferably less than about 20,000 kDa, to pass through. In other words, the molecular weight cut-off (MWCO) is above 8,000 kDa, preferably above 10,000 kDa, more preferably above 20,000 kDa. As a consequence, erythrocytes, leukocytes and thrombocytes are retained, but blood plasma components are not retained.

In a preferred embodiment, the average pore diameter or mean flow diameter of the whole blood hollow fiber membrane filter medium of the invention is in the range from about 50 nm to about 1,500 nm, preferably from about 50 nm to about 1,300 nm, more preferably from about 70 nm to about 1,250 nm.

In terms of the prevention of hemolysis, it is preferred that the average pore diameter is in the range of from about 50 nm to about 500 nm, preferably from about 50 nm to about 300 nm, more preferably from about 70 nm to about 200 nm.

In terms of ensuring permeability to blood plasma or serum, it is preferred that the average pore diameter is in the range of from about 200 nm to about 1,500 nm, preferably from about 350 to about 1,300 nm, more preferably from about 400 nm to about 1,300 nm, most preferably from about 600 nm to about 1,250, particularly preferably from about 1,000 nm to about 1,250 nm.

An advantageous range for the average pore diameter in terms of both properties may therefore be from about 150 nm to about 1,000 nm, preferably from about 200 nm to about 600 nm.

In a preferred embodiment, the whole blood hollow fiber membrane filter medium according to the present invention comprises a polymeric material, which is preferably selected from the group consisting of polyacrylonitrile, polypropylene, polyamide, polysulfone, polyvinyldifluoride, and polyethersulfone, more preferably selected from the group consisting of polyacrylonitrile, polypropylene, polyamide, polyvinyldifluoride and polyethersulfone, and most preferably selected from the group consisting of polyethersulfone and polypropylene.

In another preferred embodiment, the whole blood hollow fiber membrane filter medium has an outer diameter of from about 0.3 mm to about 3.0 mm, preferably from about 0.4 mm to about 2.5 mm, more preferably from about 0.4 mm to about 2.0 mm.

In yet another preferred embodiment, the whole blood hollow fiber membrane filter medium has an inner diameter of from about 0.2 mm to about 2.5 mm, preferably from about 0.3 mm to about 2.0 mm, more preferably from about 0.3 mm to about 1.8 mm, provided that the inner diameter is lower than the outer diameter.

It is particularly preferred that the whole blood hollow fiber membrane filter medium has an outer diameter of from about 0.4 mm to about 2.0 mm and an inner diameter of from about 0.3 mm to about 1.8 mm.

In a preferred embodiment, the ratio of the outer diameter $D_o$ of the whole blood hollow fiber membrane filter medium to the inner diameter $D_i$ of the whole blood hollow fiber membrane filter medium, i.e. $D_o/D_i$, is in the range of from about 1.0 to about 2.0, preferably from about 1.2 to about 2.0, more preferably from about 1.3 to about 1.5.

In yet another preferred embodiment, the whole blood hollow fiber membrane filter medium has a wall thickness of about 0.05 mm to about 1.0 mm, preferably about 0.05 mm to about 0.8 mm, more preferably from about 0.05 mm to about 0.5 mm.

In yet another preferred embodiment, the whole blood hollow fiber membrane filter medium has a length of about 0.5 cm to about 8 cm. Preferably, a single whole blood hollow fiber membrane filter medium of this length has a filter area of from about 3 mm² to about 500 mm², preferably from about 10 mm² to about 450 mm², more preferably from about 100 mm² to about 300 mm² concerning one single hollow fiber membrane.

The filter area is the cross section area which is covered by the feed flow in a filtration process. In the case of hollow fiber membrane filter media in an out-in filtration mode, it is the macroscopic cylindrical outer surface of all hollow fiber membranes in a filter module which is wetted by the feed flow, i.e., the whole blood for the purpose of the present invention. In the case of hollow fiber membrane filter media in an in-out filtration mode, it is the macroscopic cylindrical inner surface of all hollow fiber membranes in a filter module which is wetted by the feed flow, i.e., the whole blood for the purpose of the present invention.

If the hollow fiber membrane filter medium is porous, the filter area is different from the total material "inner" surface as the total material surface comprises the surfaces of all pores within the volume of the filter medium.

Accordingly, the structure of the whole blood hollow fiber membrane filter medium is additionally characterized by a porosity, which is preferably from about 30% to about 90%, more preferably from about 40% to about 85%, most preferably from about 43% to about 80%.

It has to be understood that the above listed preferred embodiments of the whole blood hollow fiber membrane filter medium regarding the pore size and structure as well as the parameters related to the size and shape of the fiber may apply to whole blood hollow fiber membrane filter medium in combination. For example, the following combinations a, b, c and d of preferred embodiments may be applicable for a whole blood hollow fiber membrane filter medium, which may be used e.g. as a cross-flow filter module as described above. The combinations are advantageous in terms of preventing hemolysis and ensuring permeability of blood plasma or serum, wherein the focus may slightly differ.

|   | Average pore diameter [nm] | Inner diameter [mm] | Outer diameter [mm] | Wall thickness [mm] | Accessible Porosity [%] |
|---|---|---|---|---|---|
| a | 50-1,500 | 0.2-2.5 | 0.3-3.0 | 0.05-1.0 | 30-90 |
| b | 50-500 | 0.3-1.8 | 0.4-2.0 | 0.05-0.5 | 40-85 |
| c | 200-1,500 | 0.3-1.8 | 0.4-2.0 | 0.05-0.5 | 40-85 |
| d | 150-1,000 | 0.3-1.8 | 0.4-2.0 | 0.05-0.5 | 40-85 |

In a further embodiment, the present invention is directed to a whole blood hollow fiber membrane filter medium including a polymeric material having a pore size ensuring permeability to blood plasma, but retaining blood cells, wherein the whole blood hollow fiber membrane filter medium is modified. A modification can be a coating of the hollow fiber membrane material, a pre-treatment or a pre-wetting e.g. a pre-wetting with subsequent drying, or even pre-wetting with subsequent usage of the membrane material in a wetted state.

For obtaining such a modified whole blood hollow fiber membrane filter medium, any one of the above described whole blood hollow fiber membrane filter media can be taken and subjected to a modification. By coating or pre-wetting, hemolysis can effectively be prevented even at higher values for the average pore diameter. Accordingly, at the same time it can be ensured that hemolysis is prevented and that the blood plasma or serum components to be analyzed are not retained in substantial amounts.

Therefore, it is particularly preferred that a whole blood hollow fiber membrane filter medium is pre-wetted or coated, preferably coated, which has an average pore diameter in the range of from about 200 nm to about 1,500 nm, preferably from about 350 nm to about 1,300 nm, more preferably from about 400 nm to about 1,300 nm, most preferably in the range of from about 600 nm to about 1,250 nm, and particularly preferably from about 1,000 nm to about 1,250 nm.

Pre-wetting is particularly advantageous when the average pore diameter or mean flow diameter of the whole blood hollow fiber membrane filter medium of the invention is in the range from about 50 nm to about 1,500 nm, preferably from about 50 nm to about 1,300 nm, more preferably from about 70 nm to about 1,250 nm.

In particular, a whole blood hollow fiber membrane filter medium according to combination c of preferred embodiments may be pre-wetted or coated, preferably coated, in order to obtain a whole blood hollow fiber membrane filter medium which effectively ensures permeability to blood plasma or serum and at the same time prevents hemolysis. However, since coating or pre-wetting is in any case advantageous for preventing hemolysis, it also has to be understood that whole blood hollow fiber membrane filter media according to other combinations of preferred embodiments, such as combinations a, b and d, may be modified according to the present invention.

In a preferred embodiment, the hydrophilic whole blood hollow fiber membrane filter medium is pre-wetted with salt solution, or a blood stabilization agent such as a heparin solution, or a combination of the foregoing. When the whole blood hollow fiber membrane filter medium has a length of from about 0.5 cm to about 8 cm, it is most preferable to use from about 0.1 ml to about 3 ml of the corresponding solutions for pre-wetting. Pre-wetting is advantageous because the pores are filled with liquid. Otherwise, the hydrophilic surface property of the polymeric material (in combination with the porosity and the pore size distribution) would lead to high capillary forces during "soaking up" of the plasma/serum and lead to rupture of blood cells. No capillary forces occur after contact with the whole blood sample when the pores are already filled with an adequate fluid.

When pre-wetting the whole blood hollow fiber membrane filter medium, it is important to choose a suitable solution with the same ion strength as plasma/serum in order to avoid hemolysis due to osmotic changes. A dilution of the plasma concentration, due to the additional fluid in the pores, and a change in the electrolyte concentration, e.g. sodium and chloride in the case of a sodium chloride solution, have to be taken into account for the subsequent plasma analysis.

Preferably, the whole blood hollow fiber membrane filter medium is pre-wetted with a sodium chloride solution, preferably an isotonic sodium chloride solution, more preferably a 0.9% sodium chloride solution (w:v, i.e. 9 g/l), and preferably not dried. It is most preferable that the whole blood hollow fiber membrane filter medium is directly used after pre-treatment, in order to avoid crystallization of sodium chloride at the surface which is called membrane scaling. Without being bound to theory, it is presently believed by the inventors that the formation of sodium chloride crystals should preferably be avoided because the sharp edges of these crystals can damage erythrocytes, thereby causing hemolysis. In a preferred embodiment, pre-wetting means dipping of the whole blood hollow fiber membrane filter medium into an adequate liquid, flushing the whole blood hollow fiber membrane filter medium with an adequate liquid or contacting the whole blood hollow fiber membrane filter medium with the liquid surface of an adequate liquid.

The whole blood hollow fiber membrane filter medium may also be pre-wetted with a heparin solution. For example, a heparin solution suitable for treatment of thrombosis, such as Fraxiparine including nadroparin calcium or heparin-sodium-25000 (ratiopharm), may be used. Preferably, one syringe with 0.8 ml heparin solution comprises nadroparin calcium 7.600 international units I.U, anta-Xa (corresponding to 95 I.U. to 130 I.U. of anti-Xa/mg). Further components may be calcium hydroxide/hydrochloride acid 10% for pH adjustment and water.

Still further, the whole blood hollow fiber membrane filter medium may be pre-wetted with a citrate buffer solution.

Still further, the whole blood hollow fiber membrane filter medium may be pre-wetted with an EDTA (ethylenediaminetetraacetic acid) buffer solution.

In case of a whole blood hollow fiber membrane filter medium with a very hydrophobic surface, like e. g. for polypropylene, it may be useful to fill the porous structure with an organic liquid which wets the surface easily, like ethanol, and then, in a second step, to replace this organic liquid in the pores with one of the aforementioned adequate liquids.

In another preferred embodiment, the whole blood hollow fiber membrane filter medium is coated. Preferably, the coating is suitable for reducing the hydrophilicity and wettability of the hydrophilic filter medium surface. By such a coating, the capillary forces, which induce hemolysis at the first contact of the porous membrane filter material with whole blood, can be reduced. Furthermore, a reduced hydrophilicity and wettability results in a reduced flux through the hollow fiber membrane filter medium during the filtration process on the other side.

In order to obtain a reduced hydrophilicity and a low wettability of the hydrophilic surface, the coatings have to increase the contact angle between aqueous droplets and the solid plane surface. Further requirements on the coating are as follows:

No plugging of pores, and therefore no film-building structure

Building up a homogeneous and stable coating layer

Hemocompatibility: No generation of hemolysis due to the chemistry and no adherence and/or cross-reactions with the plasma/serum analytes.

This can be achieved with e.g. fluorine-containing coating materials (e.g. products from the product line "Dynasylan" from Evonik Industries or products from the product line "Nuva" from Clariant), such as bifunctional silanes with hydrolyzable inorganic ethoxysilyl and fluoroalkyl chains (e.g. available under the trade name DYNASYLAN® F 8261 from Evonik Industries) or fluoroalkyl-functional oligosiloxanes (e.g. available under the trade name DYNASYLAN® F 8815 from Evonik Industries) for dip coating. Coating out of the gas phase is also possible with a plasma enhanced coating technology or with a sol-gel technology. Fluorine-containing molecules have the advantage that they not only establish a reduced hydrophilicity of the surface, but also an oleophobic property. This reduces the risk of adherence for non-polar substances like proteins and lipids. The extent of the reduction of hydrophilicity and the increase of oleophobicity is not only dependent on the coating substance but also on its concentration in the coating liquid (or gas), when the coating is applied, as well as on the coating process parameters, like coating procedure, temperature and contact time.

Different methods can be performed to apply the coating to a surface. A procedure for coating a porous ceramic material with e.g. fluorosilanes to obtain a reduced hydrophilicity of the surface is e.g. described in DE 19937325 B4.

For the sake of completeness, it has to be mentioned that also hydrophobic surfaces may be adapted to achieve an adequate degree of wettability. It is also possible to increase the wettability with the aforementioned coating processes.

In in-out cross-flow filtration, the coating is especially necessary at the inner filter area of the whole blood hollow fiber membrane filter medium, where the blood contacts the membrane material first. Preferably, the coating may be applied by using a dip coating procedure with a coating liquid, wherein the fluorine coating product is e.g. dissolved in an additional solvent. It is possible to dilute the coating product with an additional solvent to adjust the extent of the reduction of the hydrophilicity. As additional solvent, ethanol or water may be used.

The coating liquid with the diluted coating substances can be applied

By dip coating

In a dead-end mode: One end of the whole blood hollow fiber membrane filter medium is sealed and the coating fluid has to pass through the pores after pressure is induced.

In an open-end mode: The coating fluid passes through the inner side of the whole blood hollow fiber membrane filter medium without the influence of pressure and therefore wets only the surface.

Additionally, a post-treatment of the coating can be performed to ensure that excess coating fluid is removed. This can be done by directly flushing the whole blood hollow fiber membrane filter media after the coating process. The selection of the flushing fluid depends on the coating material itself. Some coatings have an aqueous basis, some are solvent-based. Apart from dipping, flushing can be also performed either dead-end or open-end. This leads to four different coating combinations for every coating solution.

For example, the inner filter area of a hollow fiber membrane filter medium of a length of about 19 cm may be coated with about 2 ml of coating liquid. This coating liquid is preferably loaded only onto the inner surface of the hollow fiber membrane filter medium by introducing a cannula into one hollow fiber opening. This loading can be done with an open-end hollow fiber where the coating liquid drains off the second opening of the hollow fiber membrane filter, or with a closed-end hollow fiber where pressure has to be induced to pump the coating liquid through the pores. To remove the supernatant coating liquid, a subsequent flushing with 2 ml of solvent is performed. In this case, the hollow fiber can also be either in an open-end or in a closed-end state.

In another preferred embodiment, the whole blood hollow fiber membrane filter medium is modified, e.g. by negatively charging its surface to improve hemocompatibility and to reduce protein adsorption on the solid surface. Preferably, the inner filter area of the whole blood hollow fiber membrane filter medium is negatively charged when the filter medium is used in an in-out cross-flow filtration.

In yet another preferred embodiment, the whole blood hollow fiber membrane filter medium is coated in that the surface, preferably the inner filter area, of the whole blood hollow fiber membrane filter medium carries at least one type of functional groups selected from the group consisting of carboxylate groups, amino groups, silane groups, and any combinations thereof to improve hemocompatibility.

In another preferred embodiment the whole blood hollow fiber membrane filter medium is modified by graft copolymerization; preferably, functional groups selected from the group consisting of carboxylate groups, amino groups, silane groups, and any combinations thereof can be added by graft copolymerization to improve hemocompatibility.

Graft copolymerization is a technology to produce polymers in which the main chain provides the basis for further polymer chains consisting of a different monomer type. In this way, a copolymer is produced where chains of a further monomer type are added in a comb-shaped manner to the main chain.

In another aspect, the present invention is directed to the use of a whole blood hollow fiber membrane filter medium as defined above, i.e. either not modified or modified, i.e. not pre-treated or pre-treated, not pre-wetted or pre-wetted, or not coated or coated, for separating blood plasma/serum from a whole blood sample. Preferably, the blood plasma/serum, which is obtained, shows no or substantially no hemolysis.

In a preferred embodiment, the blood plasma/serum is separated from the whole blood sample by cross-flow-filtration by using any one of the whole blood hollow fiber membrane filter media according to the present invention described above.

Preferably, cross-flow filtration is performed by passing the whole blood along the longitudinal extension of the whole blood hollow fiber membrane filter medium, optionally alternately in both directions, by applying positive pressure in respect of ambient pressure, preferably positive pressure from about 0.5 bar to about 1.5 bar. Most preferably, the positive pressure is about 0.5 bar.

Alternatively, cross-flow filtration is performed by passing the whole blood along the longitudinal extension of the whole blood hollow fiber membrane filter medium, optionally alternately in both directions, by applying negative pressure in respect of ambient pressure, preferably negative pressure from about 0.5 bar to about 1.0 bar. Most preferably, the negative pressure is about 0.5 bar.

According to the present invention, cross-flow filtration may be performed as in-out cross-flow filtration or out-in cross-flow filtration, preferably as in-out cross-flow filtration.

The present invention is directed to the use of any one of the whole blood hollow fiber membrane filter media as defined above, i.e. either not modified or modified, for separating blood plasma/serum from a whole blood sample, wherein the whole blood sample is diluted with isotonic sodium chloride solution. Preferably, the whole blood sample is diluted with isotonic sodium chloride solution, preferably with a 0.9% sodium chloride solution (w:v), in a ratio of from 0.5:1 to 1:5, preferably in a ratio of from 1:1 to 1:4.

Furthermore, the present invention is directed to the use of any one of the whole blood hollow fiber membrane filter media as defined above, i.e. either not modified or modified, for separating blood plasma from a whole blood sample, wherein the whole blood sample is stabilized with an anti-coagulation agent selected from the group consisting of EDTA, citrate, heparin and combinations thereof.

Moreover, the present invention is directed to the use of any one of the whole blood hollow fiber membrane filter media as defined above, i.e. either not modified or modified, for separating blood plasma/serum from a whole blood sample, wherein the whole blood is pre-treated with a cell agglomeration agent, such as lectin.

It should be emphasized that the use of the whole blood hollow fiber membrane filter medium as defined above is particularly advantageous for separation processes such as the separation of blood plasma/serum from a whole blood sample when used by manually operating it because, in contrast to the use of a centrifuge, the use of the whole blood hollow fiber membrane filter medium is then possible without electricity. Furthermore the use of the whole blood hollow fiber membrane filter medium is advantageous over the use of a centrifuge because it is less time consuming.

The whole blood hollow fiber membrane filter media according to the present invention may also be used as a solid-liquid or liquid-liquid separation tools in other fields, e.g. in veterinary medicine, food technology, environmental sciences, and in scientific laboratories in general. In particular, the whole blood hollow fiber membrane filter media can be used in efficient and mild separation methods of highly concentrated suspensions, cellular systems and sensitive particulate systems. It is highly preferred to use the whole blood hollow fiber membrane filter media according to the present invention in filtration processes, wherein the volume of the sample to be separated and the volume of the filtrate is small, e.g. less than 20 ml, preferably less than 10 ml, which is e.g. the case in the analytical quality assurance in production processes.

While specific embodiments of the invention have been shown and described in detail to illustrate the inventive principles, it will be understood that the invention may be embodied otherwise without departing from such principles.

What is claimed is:

1. A whole blood hollow fiber membrane filter medium including:
    a polymeric material having pores of a pore size that ensures permeability to blood plasma or serum but retains blood cells;
    wherein at least a radially inner surface of the whole blood hollow fiber membrane filter medium is coated to carry at least one type of functional groups from the silane groups, to improve hemocompatibility;
    wherein the whole blood hollow fiber membrane filter medium is a filter membrane filter medium which has been modified by graft copolymerization of at least two functional groups consisting of: carboxylate groups, amino groups, and silane groups to provide a completed filter membrane filter medium; and
    a fluorine-containing coating material having bifunctional silanes with hydrolysable inorganic ethoxysilyl and fluoroalkyl chains or fluoroalkyl-functional oligosiloxanes coated on an exterior of the completed filter membrane filter medium.

2. The whole blood hollow fiber membrane filter medium according to claim 1, wherein
    the whole blood hollow fiber membrane filter medium consists of the polymeric material.

3. The whole blood hollow fiber membrane filter medium according to claim 2, wherein
    the pore size of the polymeric material ensures permeability to blood plasma but retains blood cells.

4. The whole blood hollow fiber membrane filter medium according to claim 1, wherein
    the pore size of the polymeric material ensures permeability to blood plasma but retains blood cells.

5. The whole blood hollow fiber membrane filter medium according to claim 1, wherein
    the pore size ensures permeability to electrolytes, lipid metabolism substances, markers, enzymes, substrates, proteins, pharmaceuticals, and vitamins.

6. The whole blood hollow fiber membrane filter medium according to claim 1, wherein
    the whole blood hollow fiber membrane filter medium is a cross-flow filter medium.

7. The whole blood hollow fiber membrane filter medium according to claim 1, wherein
    the whole blood hollow fiber membrane filter medium is a dead-end filter medium.

8. The whole blood hollow fiber membrane filter medium according to claim 1, wherein
    both ends of the whole blood hollow fiber membrane filter medium are open.

9. The whole blood hollow fiber membrane filter medium according to claim 1, wherein
    the pore size allows molecules of less than about 10,000 kDa to pass.

10. The whole blood hollow fiber membrane filter medium according to claim 1, wherein
    the pores have an average pore diameter or a mean flow diameter in a range of from about 50 nm to about 1,500 nm.

11. The whole blood hollow fiber membrane filter medium according to claim 1, wherein
    the polymeric material further includes polymeric material selected from the group consisting of polyvinyldifluoride, and polyethersulfone.

12. The whole blood hollow fiber membrane filter medium according to claim 1, wherein
    the whole blood hollow fiber membrane filter medium has an outer diameter Do of from about 0.3 mm to about 3.0 mm.

13. The whole blood hollow fiber membrane filter medium according to claim 12, wherein
    the whole blood hollow fiber membrane filter medium has an inner diameter Di, wherein the inner diameter Di is from about 0.2 mm to about 2.5 mm, provided that the inner diameter Di is smaller than the outer diameter Do.

14. The whole blood hollow fiber membrane filter medium according to claim 13, wherein
    a ratio Do/Di of the outer diameter Do to the inner diameter Di is in a range of from about 1.0 to about 2.0.

15. The whole blood hollow fiber membrane filter medium according to claim 13, wherein
    the outer diameter Do is from about 0.4 mm to about 2.0 mm and the inner diameter Di is from about 0.3 mm to about 1.8 mm.

16. The whole blood hollow fiber membrane filter medium according to claim 1, wherein
    the whole blood hollow fiber membrane filter medium has a wall thickness of about 0.05 mm to about 1.0 mm.

17. The whole blood hollow fiber membrane filter medium according to claim 1, wherein
    the whole blood hollow fiber membrane filter medium in the form of a single hollow fiber membrane has a length of 0.5 cm to 8 cm and a filtration area of from about 3 $mm^2$ to about 500 $mm^2$.

18. The whole blood hollow fiber membrane filter medium according to claim 1, wherein
    the whole blood hollow fiber membrane filter medium has a porosity of from about 40% to about 85%.

19. The whole blood hollow fiber membrane filter medium according to claim 1, wherein
    the whole blood hollow fiber membrane filter medium is pre-wetted with a salt solution, a solution of a blood stabilization agent, or a combination of a salt solution and a solution of a blood stabilization agent.

20. The whole blood hollow fiber membrane filter medium according to claim 1, wherein
    the whole blood hollow fiber membrane filter medium is pre-wetted with a sodium chloride solution and is not dried after pre-wetting, wherein the sodium chloride solution is an isotonic sodium chloride solution or a 0.9% sodium chloride solution (w:v).

21. The whole blood hollow fiber membrane filter medium according to claim 1, wherein
    the whole blood hollow fiber membrane filter medium is pre-wetted with a heparin solution.

22. The whole blood hollow fiber membrane filter medium according to claim 1, wherein
the whole blood hollow fiber membrane filter medium is coated with a citrate buffer solution.

23. The whole blood hollow fiber membrane filter medium according to claim 1, wherein
the whole blood hollow fiber membrane filter medium is obtained by a phase inversion process from a spinning dope, the spinning dope including at least one polymeric material and at least one solvent and optionally at least one additive.

24. The whole blood hollow fiber membrane filter medium according to claim 23, wherein
the spinning dope is made from a polymeric granulate material including polyethersulfone, wherein the at least one solvent is n-methyl-pyrrolidone, wherein the spinning dope is conducted through an annulus cross-section of a nozzle to give the shape of the fiber,
wherein the at least one additive is a viscosity adjustment additive or a membrane pore stabilization additive.

25. A method of separating blood plasma/serum from a whole blood sample, the method including:
providing a whole blood hollow fiber membrane filter medium according to claim 1;
filtering a whole blood sample with the whole blood hollow fiber membrane filter medium so that blood plasma or serum passes through the whole blood hollow fiber membrane filter medium and blood cells are retained.

26. The method according to claim 25, wherein
the blood plasma/serum shows no or substantially no hemolysis.

27. The method according to claim 25, wherein
filtering is carried out by cross-flow filtration.

28. The method according to claim 27, the cross-flow filtration including
passing the whole blood along a longitudinal extension of the whole blood hollow fiber membrane filter medium, optionally alternately in both directions of the longitudinal extension, by applying positive pressure or by applying negative pressure.

29. The method according to claim 28, wherein
the positive pressure or the negative pressure is in a range from about 0.5 bar to about 1.0 bar.

30. The method according to claim 27, the cross-flow filtration being performed as in-out cross-flow filtration or out-in cross-flow filtration.

31. The method according to claim 25, including diluting the whole blood sample with isotonic sodium chloride solution in a ratio of from 0.5:1 to 1:5 with a 0.9% sodium chloride solution (w:v).

32. The method according to claim 25, including stabilizing the whole blood sample with an anti-coagulation agent selected from the group consisting of EDTA, citrate, heparin, and combinations thereof.

33. The method according to claim 25, including
pre-treating the whole blood sample with lectin or another cell agglomeration agent.

34. The method according to claim 25, including stabilizing the whole blood sample with citrate as an anti-coagulation agent.

* * * * *